United States Patent [19]

Miller, Jr. et al.

[11] Patent Number: 4,567,753
[45] Date of Patent: Feb. 4, 1986

[54] INDEPENDENT ANALYSIS OF ANIONS AND CATIONS USING INDIRECT PHOTOMETRIC CHROMATOGRAPHY

[75] Inventors: Theodore E. Miller, Jr.; Ziad Iskandarani, both of Midland, Mich.

[73] Assignee: The Dow Chemical Company, Midland, Mich.

[21] Appl. No.: 682,032

[22] Filed: Dec. 12, 1984

[51] Int. Cl.$^4$ .......................................... G01N 31/04
[52] U.S. Cl. .................................. 73/61.1 C; 356/72; 436/161
[58] Field of Search ....................... 73/61.1 C; 422/70; 436/161; 356/72

[56] References Cited

U.S. PATENT DOCUMENTS

| | | | |
|---|---|---|---|
| 3,918,906 | 11/1975 | Small et al. ................... | 73/61.1 C X |
| 3,920,397 | 11/1975 | Small et al. . | |
| 4,017,262 | 4/1977 | Small et al. ................... | 73/61.1 C X |
| 4,265,634 | 5/1981 | Pohl .............................. | 73/61.1 C X |
| 4,367,041 | 1/1983 | Webb, Jr. et al. ............ | 73/61.1 C X |
| 4,383,047 | 5/1983 | Stevens et al. ............... | 521/28 |
| 4,414,842 | 11/1983 | Small et al. ................... | 73/61.1 C |
| 4,455,084 | 6/1984 | Webb, Jr. et al. ............ | 73/61.1 C X |

OTHER PUBLICATIONS

H. Small and T. E. Miller, *Anal. Chem.*, 54 (1982), 462–469, "Indirect Photometric Chromatography".
"Novel Ion Exchange Chromatographic Method Using Conductimetric Detection", H. Small, T. S. Stevens and W. C. Bauman, *Anal. Chem.*, 47, (1975), 1801–1809.
"Hollow Fiber Ion-Exchange Suppressor for Ion Chromatography", T. S. Stevens, J. C. Davis, and H. Small, *Anal. Chem.*, 53, (1981), 1488–1492.
"High Performance Liquid Chromatography of Inorganic and Organic Ions . . . Detection", P. R. Haddad and A. L. Heckenberg, *J. Chromatogr.*, 252, (1982), 177–184.
"High Performance Liquid Chromatography of Ions, I. Molnar, H. H. Nauer and D. Wilk, *J. Chromatogr.*, 201, (1980), 225–240.
"Separation of Inorganic and Organic Anions on Reversed-Phase . . . Columns", N. E. Skelly, *Anal. Chem.*, 54, (1982), 712–715.
B. Sachok, S. N. Deming and B. A. Bidlingmeyer, *Journal of Liquid Chromatography*, 5(3), (1982), 389–402, "Quantitation of Alkyl Sulfonates Using UV Detector . . . Chromatography".
M. Yamamoto, H. Yamamoto and Y. Yamamoto, *Anal. Chem.*, 56, (1984), 832–834, "Simultaneous Determination of Inorganic Anions and Cations by Ion . . . Eluent".
D. R. Jenke, *Anal. Chem.*, 56, No. 13, (1984), 2468–2470, "Standardization of Transparent Analyte Response in Indirect Photometric Chromatography".
R. C. Kong, B. Sachok and S. N. Deming, *Journal of Chromatography*, 199, (1980), 307–316, "Combined Effects of pH and Surface-Active-Ion Concentration in Reversed . . . Chromatography".
C. A. Pohl and E. L. Johnson, *Journal of Chromatographic Science*, 18, (1980), 442–452, "Ion Chromatography-The State-of-the-Art".
B. A. Bidlingmeyer, *Journal of Chromatographic Science*, 18, Oct. (1980), 525–537, "Separation of Ionic Compounds by Reversed-Phase Liquid Chromatography . . . Techniques".
E. Heftmann, *Chromatography*, Third Edition, "A Laboratory Handbook of Chromatographic and Electrophoretic Methods".

Primary Examiner—Jerry W. Myracle
Assistant Examiner—Joseph W. Roskos

[57] ABSTRACT

An improved technique and apparatus for the independent measurement of anions and cations in solution, wherein the sample ions are chromatographically displaced in a plurality of ion exchange columns by an eluting ion which is or is made light-absorbing and wherein the sample ions are detectable from decrements in absorbance of the eluting ions as revealed by photometric monitoring; and the sample ions, cations and anions, are further detected independently by means for monitoring eluting anion and cation absorbance differences calibrated according to characteristic absorbance ratios of the selected eluting ion species at a plurality of wavelengths.

14 Claims, 10 Drawing Figures (240 nm)  V (mL)

(270 nm)  V (mL)

INDEPENDENT ANALYSIS OF ANIONS AND CATIONS USING INDIRECT PHOTOMETRIC CHROMATOGRAPHY

FIELD OF THE INVENTION

This invention is in the field of ion exchange chromatography. It particularly concerns a method and apparatus for the independent analysis of coeluting sample anions and cations in a liquid effluent using Indirect Photometric Chromatographic (IPC) techniques.

BACKGROUND OF THE INVENTION

Liquid chromatography is used to separate the components of a sample substance by passing an eluent containing the sample through a column. The components of the sample in the eluent stream have different retention times within the column, and therefore exit the column in a particular sequence depending on the nature of the components of the sample and the nature of the column. The sequence of components is detected, for example, photometrically by measuring the intensity of light absorbed by the eluent stream.

Developments in liquid chromatography have led beyond component separation and analysis to ion separation and analysis. Ion exchange liquid chromatography is often complicated by limitations in the capability to detect the eluted sample ions in the column effluent. For example, many inorganic and organic ions are non light-absorbing and difficult to detect using conventional photometric detectors. Even though the separation of such "transparent" ions may be conveniently effected using ion exchange resin columns, the detection and measurement of these transparent ions by conventional photometric means is ineffective since they are optically indistinguishable from the transparent eluents commonly prescribed by the art. Hence, practices using photometers to detect ions in effluent have been effective only when the ions to be analyzed either contain chromophores or can generate chromophores through post-column reactions with appropriate reagents.

The problems of transparent ion detection are in part solved by the recent development of Indirect Photometric Chromatography (IPC). IPC has been described in detail in U.S. Pat. No. 4,414,842. IPC involves a method and apparatus for measuring ions in a sample undergoing chromatographic analysis wherein the ions of interest are transparent at the wavelengths monitored by the photometer. In the IPC method, these ions are first displaced from the ion exchange column in which they have been selectively adsorbed, by passing through the column, an eluent containing eluting ions which are or are made light absorbing. The displaced sample ions as they appear in the eluent are then detected in series and quantified by observing the decrements the ions cause in eluent absorbance, as revealed by photometric monitoring. For further details of IPC principles and techniques, see, "Indirect Photometric Chromatography", $Anal.$ $Chem.$, 1982, 54, 462–469, written by Small and Miller. Both of the above references are incorporated herein.

A problem with the known IPC method arises when an attempt is made to carry out independent analysis of both anions and cations, both of which are transparent. Since such ions in the mobile or eluent phase both contribute to the absorbance of UV wavelengths, it has not heretofore been found possible to measure independently, the eluent absorbance due to the individual anions and the individual cations.

One attempt was made to detect and record anions and cations eluting simultaneously from a column; see Yamamoto, Yamamoto, Yamamoto, Matsushita, Baba and Ikushige, "Simultaneous Determination of Inorganic Anions and Cations by Ion Chromatography with Ethylenediaminetetraacetic Acid as Eluent" $Anal.$ $Chem,$ 56, 832–834, (1984). This attempt was not successful in independently determining the anion and cation concentrations as they eluted. The scientists noted that, "The retention times observed for $Ca^{2+}$ and $Mg^{2+}$, injected as metal cations, and those injected as EDTA chelate anions were not significantly different." To overcome this problem, the scientists converted the $Mg^{2+}$ and $Ca^{2+}$ cations to chelate anions using the EDTA eluent, separated the anion species for detection, and detected the anions using conventional chromatographic methods. The scientists specifically noted that $Mg^{2+}$ and $Ca^{2+}$ could not be found except as corresponding anion peaks in the chromatogram.

Even though detection systems have been developed for differentiating among pure components of an eluent stream, e.g., see U.S. Pat. No. 4,367,041, no detection system presently exists which can distinguish between transparent anion and cation species having identical or nearly identical retention times.

The present invention has as its object to provide a method and apparatus using indirect photometric chromatography techniques to detect independently anion and cation species of a sample within a single chromatograph even when the species have identical or nearly identical retention times. The technique of the present invention displaces sample anions and cations with photometrically monitorable eluent anion and cation species. The present invention teaches the use of an eluent containing a salt with chromophoric anion and cation species each having a known characteristic ratio of absorbance at predetermined wavelengths, and the use of certain mathematical equations to develop, independently two chromatograms, one for anions, and one for cations.

Other objects, features and advantages of the present invention will become apparent upon reading the following detailed description and examples, when taken together with the drawing and appended claims.

SUMMARY OF THE INVENTION

The invention relates to a method and apparatus for detecting independently photometrically indetectable sample anions and cations using an anion exchange stationary phase and a cation exchange stationary phase, an Indirect Photometric Chromatography method of detection, a particular kind of anion and cation displacing eluent, a multiple analysis wavelength detector, circuitry for mathematically manipulating data, and a recording means.

The method of the invention in a preferred form involves the steps of:

(a) determining inherent relative absorbance ratios for the ions of the eluent, i.e., the ratio for the anions of a particular eluent at selected first and second wavelengths and the ratio for the cations of a particular eluent at the selected first and second wavelengths;

(b) forming a stream of eluent using an eluent comprising a soluble salt solution having: (1) chromophoric monitor/displacing anions and cations capable of producing distinctive ratios of absorbance wavelengths and (2) a pH compatible with a first ion exchange stationary phase and a second ion exchange stationary phase and flowing the stream through the first ion exchange stationary phase and the second ion exchange stationary phase to a detector;

(c) introducing a sample into the stream of eluent and flowing the sample with the eluent to the first ion exchange stationary phase;

(d) displacing ions of the sample having a common charge with eluent ions having a similar change using said first ion exchange stationary phase and forming an effluent;

(e) flowing the effluent from the first ion exchange stationary phase into the second ion exchange stationary phase and displacing the ions of the sample having a common charge opposite the charge of the sample ions of the preceding step (d) with eluent ions having a similar charge;

(f) detecting the total absorbance values for the effluent at a first wavelength and at a second wavelength;

(g) passing the detected total absorbance values from the detector to circuitry for determining the concentration of cations in coeluting anion-cation sample bands by multiplying the inherent relative absorbance ratio for the eluent anion with the total effluent anion and cation absorbance detected at the first wavelength and subtracting the total effluent anion and cation absorbance detected at the second wavelength to eliminate the effect of fluctuations in eluent anion concentrations and to reveal fluctuations in eluent cation concentrations and fluctuations in sample cation concentrations; and determining the concentration of anions in coeluting anion-cation sample bands by multiplying the inherent relative absorbance ratio for the eluent cation with the total effluent anion and cation absorbance value detected at the first wavelength and subtracting the total effluent anion and cation absorbance value detected at the second wavelength to eliminate the effect of fluctuations in eluent cation concentrations and to reveal fluctuations in eluent anion concentrations and fluctuations in sample anion concentrations; and (i) recording the individual responses corresponding to the anions and cations of the sample.

Generally described, the present invention provides a method and apparatus for independently detecting photometrically indetectable anions and cations of a sample, regardless of the concentration of the sample, by chromatographically displacing the anions and cations of the sample using indirect photometric chromatography techniques. It should be noted that the phrase "regardless of the concentration of the sample" refers to concentrations of sample within normal chromatographic limitations. Eluent anions and cations, once photometrically detected, reveal the anion and cation of the sample by detection of the decrements caused in effluent absorbance of the eluent anions and cations when subjected to photometric monitoring at two preselected wavelengths, $\lambda_1$ and $\lambda_2$.

This method and apparatus invention is predicated on the existence of characteristic absorption spectra for the components of a selected eluent. More specifically, this invention is based on the fact that for a set of wavelengths, an eluent containing a single salt will exhibit constant absorptivity ratios, each distinctive for the anion and cation of the eluent salt. Each constant ratio is referred to hereafter as the "inherent relative absorbance ratio."

The general formula used in accordance with the principles and teachings of the invention is:

$$A_d = RA_{\lambda_1} - A_{\lambda_2}$$

wherein $A_d$, $A_{\lambda_1}$, and $A_{\lambda_2}$ and absorbance signals, and R is the inherent relative absorbance ratio for either an eluent anion or an eluent cation depending on the ion being measured. More specifically, if sample cations are to be measured then R is computed using the general formula:

$$R = (A_{\lambda_2}^- / A_{\lambda_1}^-)$$

where $A_{\lambda_1}^-$, represents the absorbance value of the anion species of the eluent at a first wavelength and $A_{\lambda_2}^-$ represents the absorbance value of the anion species at a second wavelength. If sample anions are to be measured, then R is computed using the general formula:

$$R = (A_{\lambda_2}^+ / A_{\lambda_1}^+)$$

For example, if the salt copper ortho-sulfobenzoate (Cu o-SB) is used in the eluent, the general formula is written as follows:

$$A_d = RA_{240} - A_{270}$$

wherein for sample anion detection $$R = (A_{270}^+ / A_{240}^+);$$

and for sample cation detection:

$$R = (A_{270}^- / A_{240}^-)$$

with wavelength values given in nanometers. Solving for the factor R for sample anion detection using experimental data, R is about 0.45, i.e., $$0.45 = (A_{270}^+ / A_{240}^+)$$

and for sample cation detection R is about 0.74, i.e., $$0.74 = (A_{270}^- / A_{240}^-)$$

These R values are determined simply by ratioing cation peaks using detected absorbance at 240 and 270 nm and anion peaks using detected absorbance at these wavelengths.

Further, when the absorbance difference signal ($A_d$) for eluent anions is zero, then $A_d$ for sample cations is determined by the equation:

$$A_d = (0.74)A_{240} - A_{270}.$$

Similarly, when the absorbance difference signal ($A_d$) for eluent cations is zero, then $A_d$ for eluent sample anions is determined by the equation:

$$A_d = (0.45)A_{240} - A_{270}.$$

A basic feature of the invention is in the use of eluent having light absorbing anion and cation species capable of chromatographically displacing anions and cations of the sample of interest.

The eluent must contain light-absorbing anions and cations which:

(1) selectively displace the sample anions and cations from the chromatographic columns or ion exchange media, and (2) reveal the sample anions and cations in the effluent.

The eluent which performs these two functions contains anions and cations which displace the transparent sample anions and cations from the column and enable the anions and cations of the sample to be detected in the column effluent as dips or troughs in the baseline absorbance of the anions and cations of the eluent.

The eluent must contain light-absorbing anions and cations which have UV or light absorption coefficients such that the anion will not completely mask the cation, or vice versa. Also, the eluent must contain anions and cations of appropriate displacing power to elute the sample ions from the column in a reasonable amount of time, i.e., allowing resolution of peaks without excessive peak broadening. An ideal eluent should contain anions and cations which exhibit absorbances of at least 0.1 AU at $10^{-3}$ molar with a path length of 1 cm at 220 nm or above.

The eluent should contain a "monitor/displacing" salt which is soluble in water and preferably either aromatic, organic, inorganic, polyvalent or monovalent, or a combination of these characteristics. Even more importantly, the eluent should not contain a second salt which may form spurious peaks upon photometric detection.

The eluent should have a pH which does not affect chromatographic column packing not destroy the ionic nature of the chromatographic column. More specifically, the eluent must not have a low pH, such as pH 1, wherein eluent hydrogen ions would begin to function as the displacing ions in place of the intended eluent ions. Similarly, the eluent must not have a high pH, e.g., pH 12, such that the eluent precipitates metal in the eluent or alternatively causes the hydroxide to act as a displacing ion. A pH of less than 7 is preferred for most silica-based ion exchange columns. Eluents with a pH in the range of pH 4 to pH 5 are effective and useful within the teachings and principles of the invention.

The apparatus of the invention involves a system for independently measuring anions and cations of a sample using indirect photometric chromatography, an eluent comprising a soluble salt solution having chromophoric anions and cations and having an inherent relative absorbance ratio for the anions of an eluent at selected first and second wavelengths and for the cations of the same eluent at the same first and second wavelengths. The invention further involves an anion exchange stationary phase, a cation exchange stationary phase and a detector connected in series. The invention includes means for forming a stream of eluent flowing through the anion exchange stationary phase and the cation exchange stationary phase to the detector. The invention involves means for introducing a sample of interest into the stream of eluent and flowing the sample and eluent through the anion exchange and cation exchange stationary phase means to produce an effluent. The detector is preferably a multiple wavelength detector with means for receiving the effluent from the ion exchange stationary phases and measuring the total absorbance of the anions and cations in the effluent at a first wavelength and a second wavelength. The apparatus invention also includes circuitry responsive to the detector with means for using the inherent relative absorbance ratios distinctive for the eluent anions and cations and the detected total absorbance values for the effluent at first and second wavelengths to determine separately sample anion and sample cation concentrations. The apparatus invention can further involve recording means for recording the individual responses corresponding to the anions and cations of the sample.

The particular circuitry of the instant invention consists of means for using the inherent relative absorbance ratio for each eluent ion to scale the detected total absorbance value of the effluent ions at a first wavelength to produce a scaled value and subtracting the detected total absorbance value of the effluent at a second wavelength from the scaled detected total absorbance value at the first wavelength to produce individual absorbance values for the eluent anion and cation, eliminating the effect of fluctuations in eluent anion and cation concentrations and subsequently revealing fluctuations in sample anion and cation concentrations.

Terms

Throughout this specification terms particular to liquid chromatography and this invention will be used. The definitions of these terms follows:

"Transparent"—This term refers to the inability or lesser ability of an anion or cation of a sample of interest to absorb light at the selected wavelengths or be photometrically detected relative to the light absorbance property of an eluent.

"Eluent"—This term refers to the mixture of the specified salt in deionized LC quality water without sample, e.g., copper ortho-sulfobenzoate in LC quality water.

"Effluent"—This term refers to the aqueous mixture which results from passing eluent through the medium capable of performing the ion exchange.

"Wavelength"—This term refers to a wavelength or a wavelength band.

"Inherent relative absorbance ratio"—This expression denotes the quotient of optical absorbances at two different specified wavelengths for a single ionic species employed in the eluent. Since spectral features are generally independent of species concentration, this ratio remains constant as the concentration of an absorbing species varies.

BRIEF DESCRIPTION OF THE DRAWINGS

The invention may be explained with reference to the accompanying drawings in which.

DESCRIPTION OF THE INVENTION

Figure 1:
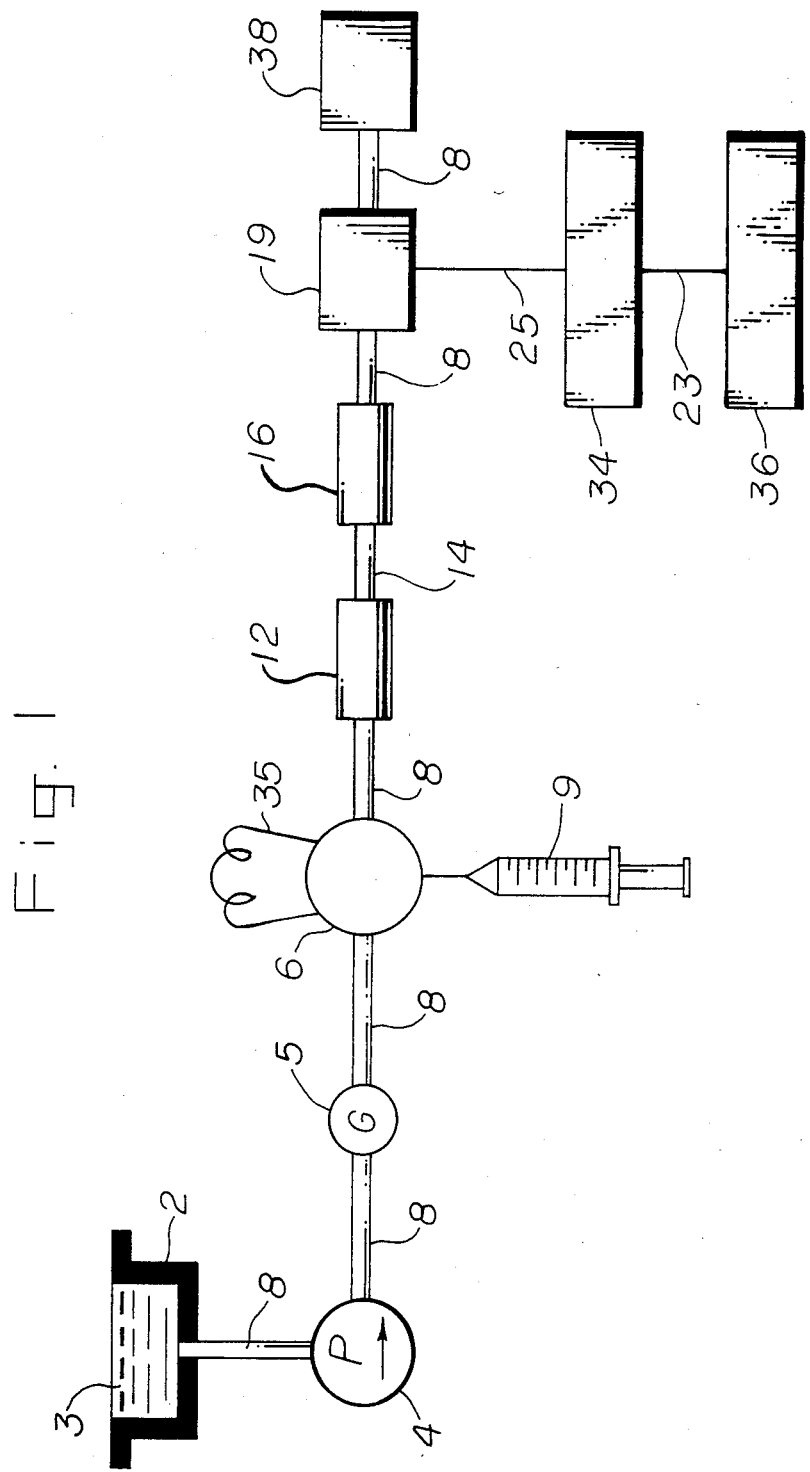
FIG. 1 is a diagram of apparatus according to the principles and teachings of the present invention.

Referring to FIG. 1, there is shown a typical diagram of an ion exchange chromatography system or apparatus which is desirably used in practicing the invention. The apparatus includes separating means such as two liquid chromatography columns 12 and 16 which are packed with media capable of performing ion exchange separations. Most chromatographic ion exchange media are in the pellicular or micro-particular form. Alternatively, the invention may employ a non-ion exchange chromatographic medium which is or can be rendered ion exchange-performing under the influence of the specified eluent. For example, a $C_{18}$ reverse phase LC column could be used as one of the preferred separating means; such as the work reported by Skelly, N. E. *Anal. Chem.*, 54, No. 4, 1982, pp. 712-715.

Columns 12 and 16 are connected to a photometric detector 19. Detector 19 is a flow-through UV photometer with micro-volume cell design for high performance liquid chromatography (HPLC) applications. Detector 19 is connected with waste vessel 38 for receiving the analyzed effluent.

Sample may be placed into the eluent stream flowing into column 12 using any suitable device but preferably using a syringe 9 to load an injection valve 6 having a sample loop 35. The injected sample is swept through column 12 and then column 16 with eluent 3 containing monitor/displacing light-absorbing anions and cations. Eluent 3 is drawn through tubing 8 from eluent reservoir 2 preferably using a chromatographic pump 4. The pressure of the eluent stream is preferably monitored by a pressure gauge 5. A first ion exchange occurs in column 12. Effluent from column 12 is passed through tubing 14 to column 16 wherein a second ion exchange appears. Effluent from column 16, containing resolved anions and cations is flowed to the photometric detector 19 through tubing 8. Tubing 8 preferably is conventional tubing with an 0.02 inch I.D. Tubing 14 is preferably a short length of 1/16 inch HPLC tubing. Photometric detector 19 is in electronic communication with circuitry 34 and recording means 36.

Additionally, pump 4 of this embodiment is a standard liquid chromatographic pump capable of operation with non-pulsing flow rates in the appropriate range. As an example, pump 4 could utilize a flow rate in the range of greater than 0.5 cc/min and less than 5 cc/min. The pump 4 is capable of providing pressure on the system within the range of 100-6000 psig.

The columns of this embodiment are preferably anion exchange and cation exchange columns connected in series as columns 12 and 16. The particular columns useful in this method and apparatus are columns with a total capacity in milliequivalents (meq) preferably in the range of $10^{-3}$ to 10 meq.

Silica columns are particularly useful in this invention. Other columns which can be used within the principles and teachings of this invention include surface sulfonated cation exchange resins and surface agglomerated latex anion exchangers with resin substrates.

These separating columns useful in this invention are preferably commercially available anion and cation exchange columns with low anion and cation exchange capacities. Preferably, the separating columns are strong anion and cation exchangers. As an example, a ZIPAX® SAX or SCX duPont column, with prepacked dimensions of 2.1 mm×500 mm is useful within the principles and teachings of this invention.

Detector 19 is preferably an ultraviolet light detector; however, another detector can be used within the scope of the invention provided the detector offers a variable parameter to selectively enhance the detectability of eluent components.

In the photometric detector 19, the absorbance of the light-absorbing eluent anions and cations is measured both at a first wavelength $\lambda_1$ and at a second wavelength $\lambda_2$. These measured absorbance values are then converted into signals which are passed by means 25 to circuitry 34 for mathematical manipulation. The circuitry 34 determines the absorbance difference values for cations and anions individually using the general formula:

$$A = RA_{\lambda_1} - A_{\lambda_2}$$

for measuring ions in the sample, wherein
$A_{\lambda_1}$ is the total absorbance of the effluent at a first wavelength;
$A_{\lambda_2}$ is the total absorbance of the effluent at a second wavelength; and
R is the known inherent absorbance ratio for a given eluent ion.

A computer may be used as the circuitry 34 to reveal the individual chromatograms or alternatively store and process the chromatographic patterns into sample ion data without recording the actual chromatograms. Similarly, the circuitry 34 can be used for sample cation chromatograms.

The data resulting from these computations then can be transmitted over means 23 to recording means 36, such as a strip chart recorder with dual tracing capabilities, or alternatively to two recorders connected in parallel, each of which is capable of recording the respective absorbance information. Recording means 36 can consist of any form of storage device, such as a computer memory, chart paper or digital readouts.

The concentrations of sample anion and cation can be determined independently and simultaneously using the above described apparatus.

The method and apparatus of the present invention require a specified eluent to achieve the objects of the invention. The preferred characteristics of the eluent are described in the subsequent paragraphs.

An ideal eluent is one which can exhibit UV absorbance spectra with a maximum absorbance wavelength for anion absorbance and a minimum absorbance wavelength for cation absorbance. Alternatively, an ideal eluent is one which can exhibit UV absorbance spectra with a minimum absorbance wavelength for anion absorbance and a maximum absorbance wavelength for cation absorbance. The eluent should have an absorbance within a range of 0.1 to 3.0 AU at the selected wavelengths. In the preferred embodiment, the eluent should exhibit an absorbance within the range of 0.5 to 1.5 AU at suitable wavelengths.

The eluent should also have UV absorbing qualities capable of revealing low concentrations of transparent anions and cations during Indirect Photometric Chromatography (IPC). An ideal eluent should contain less than about $5\times10^{-2}$ molar of displacing anions and cations for the purpose of sensitive detection using the IPC method of analysis. A preferred molarity for the eluent is within the range of $5\times10^{-5}$ to $5\times10^{-2}$ molar, ideally between $5\times10^{-5}$ to $5\times10^{-3}$.

An ideal eluent has an eluting power such that it produces a sample ion k' within the range of 0.5 to 50 at eluent concentrations ranging from $10^{-5}$ to $10^{-1}$ molar. A preferred eluent develops k' within the range of 1 to 20 at concentrations ranging from $10^{-5}$ to $10^{-2}$ molar. (k' refers to the expression:

$$(V_E - V)/V,$$

where $V_E$ equals sample ion elution volume and V is the void volume).

In a preferred embodiment, the eluent of the instant invention should be capable of being easily prepared from analytical grade reagents and capable of being prepared so that no secondary salt is present. One such preferred eluent, which exhibits two different absorption spectra for its anion and cation, is easily prepared from analytical reagent grade ortho-sulfobenzoic acid cyclic anhydride (o-SBA) and copper (II) hydroxide. This preferred eluent comprises copper ortho-sulfobenzoate having the structural formula:

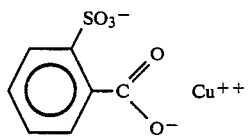

A particularly effective eluent salt is one which is multivalent, aromatic, and with a high molecular weight. Effective eluents are prepared by dissolving weighed amounts of the salts in deionized LC quality water. As an example, copper ortho-sulfobenzoate can be prepared by dissolving known weights of o-SBA cyclic anhydride and $Cu(OH)_2$ in deionized water to give the required equi-normal concentrations.

Other eluents which meet these criteria include benzyl-trimethylammonium nitrate. Benzyl-trimethylammonium eluent cation, ($BTA^+$), exhibits an inherent relative absorbance ratio of about 5.13 for sample anion detection, i.e., $$R=(A_{260}{}^+/A_{230}{}^+)=5.13$$

For sample cation detection, nitrate eluent anion, ($NO_3{}^-$), exhibits an inherent relative absorbance ratio of about 0.025, i.e., $$R=(A_{260}{}^-/A_{230}{}^-)=0.025$$

It should be noted that the monovalency of both eluent species tends to reduce the sensitivity of detection compared to that of divalent $Cu^{++}$ o-SB$^=$ which can be employed at lower eluent concentrations. Also $BTA^+$ exhibits a disproportionately strong sample eluting power relative to nitrate.

Another eluent is copper nitrate $(Cu^{+2}(NO_3{}^-)_2)$. $Cu^{+2}$ exhibits an inherent relative absorbance ratio of 0.248 for sample anion detection, i.e., $$R=(A_{263}{}^+/A_{233}{}^+)=0.248$$

For sample cation detection, nitrate, the eluent anion, exhibits an inherent relative absorbance ratio of 0.031 at these same wavelengths, i.e., $$R=(A_{263}{}^-/A_{233}{}^-)=0.031$$

For this eluent, the equi-normal nitrate is very weak as a displacing ion relative to divalent copper and the sample anions are highly retained relative to sample cations.

Additional eluents that have been considered include copper phthalate, copper trimesate, copper iodide, and pyridinium (aromatic cation) salts. In each of these cases, spectral data shows that one ion of the pair would exhibit an extreme degree of optical absorbance relative to the other, masking the counterion's absorbance at every wavelength.

Benzyltrimethyl ammonium iodide ($BTA^+$ $I^-$) would be expected to be suitable using 250 and 270 nm detection wavelengths but monovalency would again be expected to limit sensitivity relative to divalent Cu o-SB.

The following examples further detail the principles and teachings of the present invention. Additional objectives, aspects and advantages of the invention will be apparent from the following examples.

EXAMPLE 1

In this example, the apparatus includes an eluent reservoir, a Laboratory Data Control (LDC) Constametric I pump, a Rheodyne Model 7010 injection valve, a duPont ZIPAX ® SAX column, and a duPont ZIPAX ® SCX column both prepacked and 2.1 mm×500 mm, a Micromeritics Model 788 dual variable wavelength detector and a Linear Model 585 dual channel recorder.

The preferred eluent is prepared from analytical reagent grade ortho-sulfobenzoic acid cyclic anhydride (o-SBA), and copper hydroxide to form a $5\times10^{-4}$ molar mobile phase copper ortho-sulfobenzoate eluent. More particularly, the $5\times10^{-4}$ molar copper ortho-sulfobenzoate eluent is prepared by dissolving 92.1 milligrams of ortho-sulfobenzoic acid cyclic anhydride (FW 184.17) and 48.8 milligrams of copper (II) hydroxide (FW 97.54) into each liter of water (LC quality water). The solution is stirred until all particles are dissolved and the pH of the eluent is measured to be in the range of pH 4 to pH 6.

Eluent is placed in the reservoir and the LDC Constametric pump draws eluent from the reservoir and pumps it to a duPont ZIPAX ® SAX column at a flow rate of about 1.0 milliliter per minute with an inlet pressure of 2200 psi for this first of the two columns in series. A 20 microliter sample aliquot containing $10^{-3}$ molar of $NH_4Cl$ and $10^{-3}$ molar $K_2SO_4$ is injected into the stream of eluent between the pump and the first column using the Rheodyne Model 7010 sample injector valve. Anion exchange occurs in the first column and effluent from the first column then proceeds into a second ZIPAX ® SCX column. The inlet pressure for the second column is approximately 1100 psi and approaches 0 psig between the inlet and outlet of this ZIPAX ® SCX column. Effluent from the SCX column is flowed into a Micromeritics Model 788 dual variable wavelength detector. In the detector, the effluent from the second column enters a cell having windows disposed at opposite ends. Light is passed from a light source through the first set of windows, the effluent, and a second set of windows to a variable angle concave grating which separates the light waves into at least two distinct wavelengths. The light beams at these wavelengths are then detected. In this example, UV detection is performed at two wavelengths, 270 and 240 nm. The instrument then passes the detected effluent absorbance values to circuitry or alternatively other means for mathematically manipulating the data relative to the general formula $A_d=RA_{\lambda 1}-A_{\lambda 2}$. The manipulated data is subsequently communicated to a Linear Model 585 multichannel recorder.

An interesting, useful feature of the invention is that sample anions and cations exhibit two different but constant ratios of peak heights or areas at 270 nm relative to 240 nm. These known inherent relative absorbance ratios are values equivalent to the ratios of the inherent molar absorptivities of $Cu^{++}$ and o-SB$^=$ at the two wavelengths, 270 nm and 240 nm, in accordance with the principles of IPC. This feature allows immediate identification of peaks as anion or cation.

Figure 2:
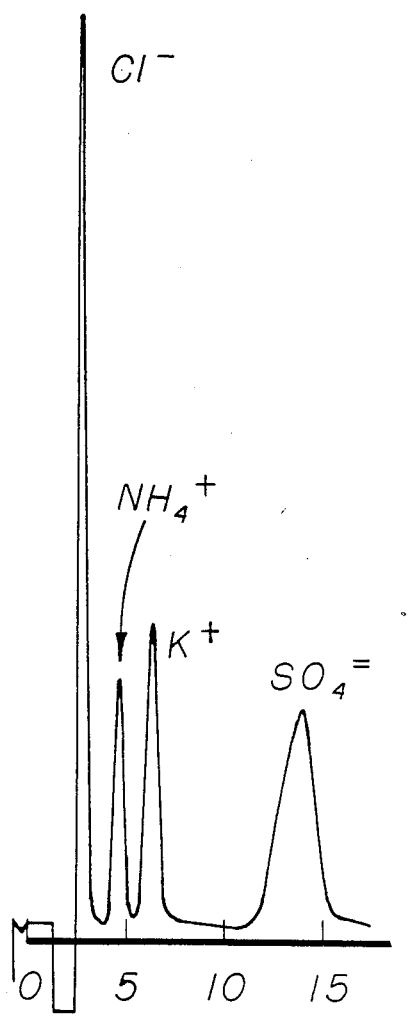
FIGS. 2 through 10 are chromatograms made using the apparatus and following the procedures in the various examples below.
Figure 3:
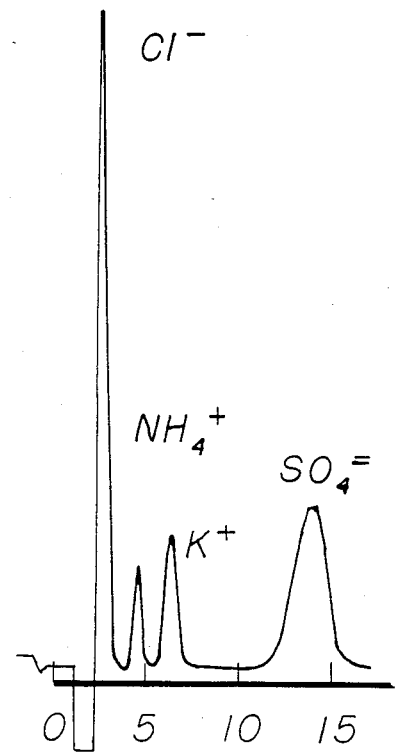
Figure 4:
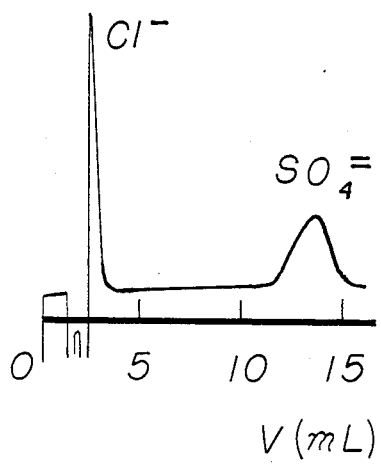
Figure 5:
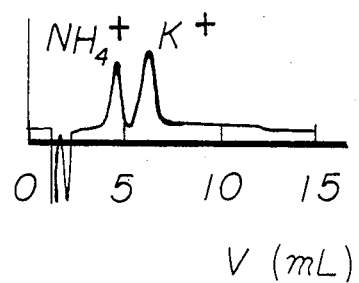
Figure 7:
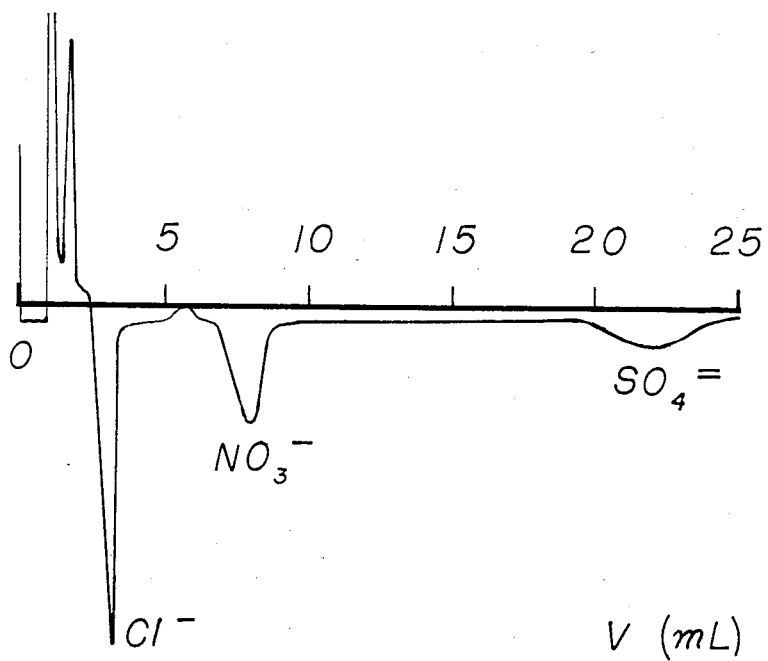
Figure 10:
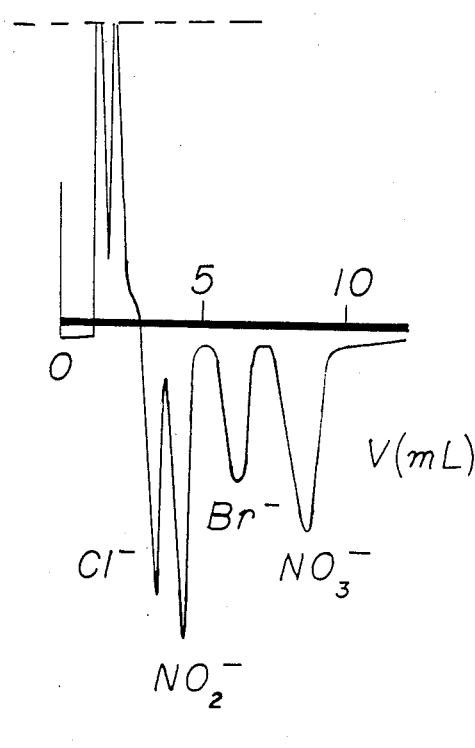

At wavelengths 270 nm and 240 nm o-SB= exhibits a constant ratio of 0.74 while Cu++ exhibits a constant ratio of 0.45. FIGS. 2-5 are the chromatograms resulting from using Cu o-SB in accordance with the parameters of Example 1. FIG. 2 is the chromatogram measured at 240 nm. FIG. 3 is the chromatogram measured at 270 nm. FIG. 4 is a chromatogram representing the detection of anions alone, i.e., $A_d = (0.45)A_{240} - A_{270}$. FIG. 5 is a chromatogram representing the detection of cations alone, wherein $A_d = (0.74)A_{240} - A_{270}$. For purposes of illustration, the FIG. 4 chromatogram is inverted. A consequence of the method is to invert the anion chromatograms as seen in FIGS. 7 and 10.

EXAMPLE 2

Figure 6:
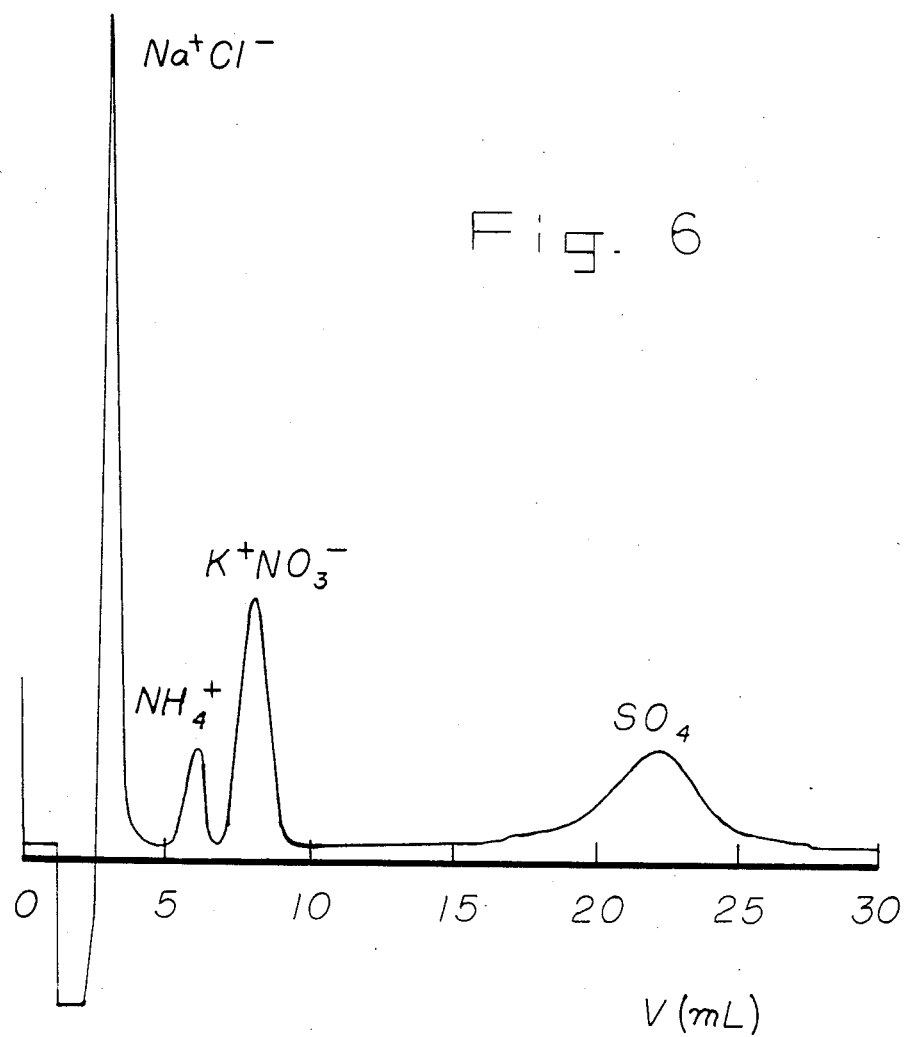
Figure 8:
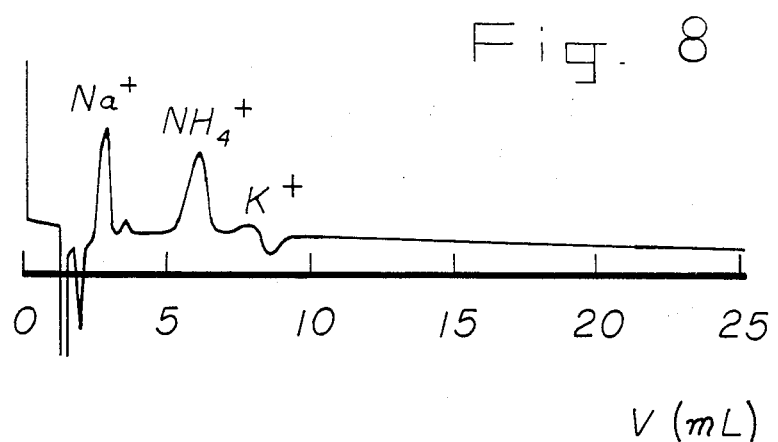

This example illustrates the separation of anions and cations of a synthetic acid rain sample ($Na^+$, $NH_4^+$, $K^+$, $Cl^-$, $NO_3^-$, $SO_4^=$) using an eluent of $2.5 \times 10^{-4}$M Cu o-SB. FIG. 6 is a chromatogram of two completely resolved peaks ($NH_4^+$, $SO_4^=$) and the coelution of the other compounds as only two peaks ($Na^+$, $Cl^-$ and $K^+$, $NO_3^-$) which are nonetheless also completely resolved by the method of the invention. Employing the method taught by this invention, the independent analysis of anions and cations results in the chromatograms of FIGS. 7 and 8, respectively. FIG. 8 shows the interference of a negative peak with the $K^+$ peak. This interference is due to the absorbance of $NO_3^-$ ion at 240 nm which results in an interference with the detection mode of IPC resulting in a peak height ratio different from 0.74. This kind of chromatographic result will occur for those few sample ions that absorb at either 270 nm or 240 nm wavelengths of detection. This peak interference difficulty is easily overcome if the sample ion is transparent at one of the detection wavelengths, as is the case with nitrite ($NO_2^-$) and nitrate ($NO_3^-$). Example 3, following, illustrates how this is accomplished.

EXAMPLE 3

Figure 9:
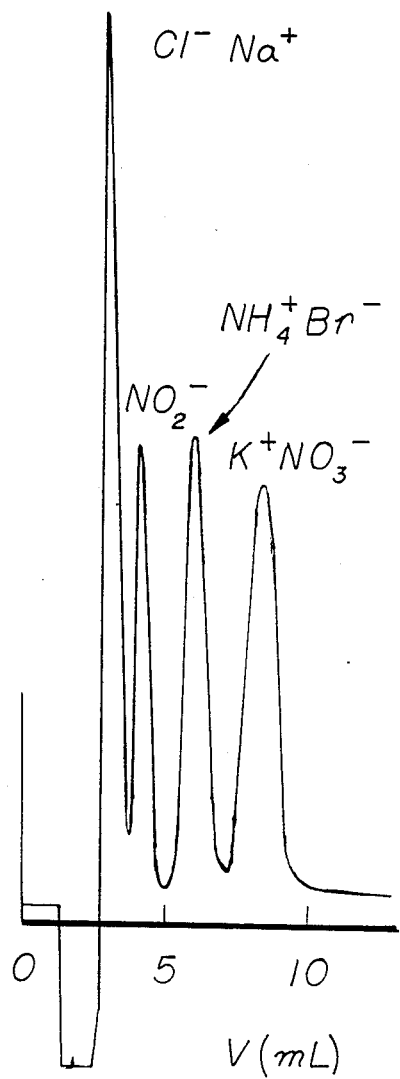

This example shows the applicability of the present invention to the chromatographic analysis of anions and cations in complex mixtures including nitrite and nitrate. Using the apparatus of Example 1, a 20 μl $10^{-3}$M sample containing $Na^+$, $NH_4^+$, $K^+$, $Cl^-$, $NO_2^-$, $Br^-$, and $NO_3^-$ is injected into the system using a mobile phase of $2.5 \times 10^{-4}$M copper ortho-sulfobenzoate. FIG. 9 shows the combined chromatogram observed at 270 nm, where both nitrite and nitrate are transparent. FIG. 10 illustrates the anion chromatogram developed using the method of the invention. The potassium ($K^+$) peak, coeluting with nitrate, is quantified from the difference in peak magnitudes between the combined peak (FIG. 9) and the nitrate peak alone (FIG. 10).

What is claimed is:

1. Apparatus for independently measuring anions and cations of a sample using indirect photometric chromatography, and using an eluent comprising a soluble salt solution having chromophoric anions and cations, the eluent having an inherent relative absorbance ratio for commonly charged ions of the eluent at selected wavelengths useful for measuring sample ions in coeluting sample bands of anions and cations, the apparatus comprising in combination:

an anion exchange stationary phase means, a cation exchange stationary phase means, and a detector connected in series;

means for forming a stream of eluent flowing through said anion exchange stationary phase means and said cation exchange stationary phase means to the detector;

means for introducing a sample into said stream of eluent for flowing said sample and eluent through said anion exchange and cation exchange stationary phase means to produce an effluent;

said detector being a multiple wavelength photometric detector with means for receiving effluent from said anion exchange and cation exchange stationary phase means and determining the total absorbance of the eluent anions and cations in said effluent at different wavelengths; and circuitry responsive to said detector with means for using the inherent relative absorbance ratio distinctive for said eluent ions and the detected total absorbance values for effluent ions at said different wavelengths to determine sample ion concentrations in overlapping anion and cation sample bands.

2. The apparatus of claim 1, comprising means for recording the individual responses corresponding to the anions and cations of the sample.

3. The apparatus of claim 1, comprising circuitry capable of determining the concentration of sample cations in overlapping anion and cation sample bands using the inherent relative absorbance ratio for the eluent anion and the detected total absorbance value of the effluent ions at a first wavelength to produce a scaled value and subtracting from that scaled value the detected total absorbance value of the effluent ions at a second wavelength to eliminate the effect of fluctuations in eluent anion concentrations and to simultaneously reveal fluctuations in eluent cation concentrations and fluctuations in sample cation concentrations.

4. The apparatus of claim 1, comprising circuitry capable of determining the concentration of sample anions in overlapping anion and cation sample bands using the inherent relative absorbance ratio for the eluent cation and the detected total absorbance value of the effluent ions at a first wavelength to produce a scaled value and subtracting from that scaled value the detected total absorbance value of the effluent ions at a second wavelength to eliminate the effect of fluctuations in eluent cation concentrations and to simultaneously reveal fluctuations in eluent anion concentrations and fluctuations in sample anion concentrations.

5. The apparatus of any of the preceding claims 1-4, using circuitry responsive to said detector with means for using the inherent relative absorbance ratios distinctive for eluent cations and anions and the detected total absorbance values for effluent ions at first and second wavelengths to determine sample cation and anion concentrations in overlapping anion and cation sample bands.

6. A method for measuring coeluting sample bands of anions and cations in liquid effluent using indirect photometric chromatography, comprising the steps of:

selecting an eluent comprising a soluble salt solution having chromophoric monitor/displacing anions and cations capable of producing distinctive ratios of absorbance useful for measuring sample ions in coeluting sample bands of anions and cations;

determining an inherent relative absorbance ratio for commonly charged ions of the eluent at first and second wavelengths;

forming a stream of said eluent and flowing said stream through a first ion exchange stationary phase means and a second ion exchange stationary phase means to a detector with the second ion exchange stationary phase means being of opposite charge to the first ion exchange stationary phase means;

introducing a sample into said stream of eluent thereby flowing the sample and eluent through the first and second ion exchange stationary phase means effective to produce effluent containing sample bands of anions and cations in solution;

detecting the total absorbance values for said effluent at a first wavelength and at a second wavelength;

using the inherent relative absorbance ratio distinctive for said commonly charged eluent ions and the total absorbance values at said first and second wavelengths to measure the concentrations of sample ions of opposite charge to said eluent ions which coelute in overlapping bands of cations and anions.

7. The method of claim 6, comprising the steps of:

determining the concentration of sample cations in overlapping anion and cation sample bands by using the inherent relative absorbance ratio for the eluent anion and the detected total absorbance value of the effluent ions at a first wavelength to produce a scaled value and subtracting from that scaled value the detected total absorbance value of the effluent ions at a second wavelength to eliminate the effect of fluctuations in eluent anion concentrations and to simultaneously reveal fluctuations in eluent cation concentrations and fluctuations in sample cation concentrations.

8. The method of claim 6, comprising the steps of:

determining the concentration of sample anions in overlapping anion and cation sample bands by using the inherent relative absorbance ratio for the eluent cation and the detected total absorbance value of the effluent ions at a first wavelength to produce a scaled value and subtracting from that scaled value the detected total absorbance value of the effluent ions at a second wavelength to eliminate the effect of fluctuations in eluent cation concentrations and to simultaneously reveal fluctuations in eluent anion concentrations and fluctuations in sample anion concentrations.

9. The method of any of the preceding claims 6-8, using the inherent relative absorbance ratios distinctive for said eluent anions and cations and the detected total absorbance values for effluent ions at first and second wavelengths to determine sample anion and cation concentrations in overlapping anion and cation sample bands.

10. The method as claimed in claim 6, further comprising the use of an eluent containing less than about $5 \times 10^{-2}$ molar of anions and cations.

11. The method as claimed in claim 6, further comprising the use of monovalent, water soluble, chromophoric eluent ions.

12. The method as claimed in claim 6, further comprising the use of polyvalent, water soluble, chromophoric eluent ions.

13. The method as claimed in claim 6, further comprising using a stream of eluent comprising a solvent and copper ortho-sulfobenzoate having a known inherent relative absorbance ratio of about 0.74 for eluent anions and about 0.45 for eluent cations for measuring sample cations and sample anions respectively.

14. The method as claimed in claim 6, further comprising using a stream of eluent comprising a solvent and benzyltrimethylammonium nitrate having a known inherent relative absorbance ratio of 0.025 for eluent anions and 5.13 for eluent cations for measuring sample cations and sample anions respectively.

* * * * *